US009717682B2

(12) United States Patent
Zerbe et al.

(10) Patent No.: US 9,717,682 B2
(45) Date of Patent: Aug. 1, 2017

(54) SOLID ORAL FILM DOSAGE FORMS AND METHODS FOR MAKING SAME

(71) Applicant: Intelgenx Corporation, Ville St. Laurent, Quebec (CA)

(72) Inventors: Horst Zerbe, Hudson (CA); Nadine Paiement, Ville St. Laurent (CA); Angela Angusti, Montreal (CA); Cormac Long, LaSalle (CA)

(73) Assignee: Intelgenx Corporation, St. Laurent (CA)

( * ) Notice: Subject to any disclaimer, the term of this patent is extended or adjusted under 35 U.S.C. 154(b) by 287 days.

(21) Appl. No.: 13/748,241

(22) Filed: Jan. 23, 2013

(65) Prior Publication Data

US 2013/0137698 A1    May 30, 2013

Related U.S. Application Data

(62) Division of application No. 12/963,132, filed on Dec. 8, 2010.

(60) Provisional application No. 61/267,626, filed on Dec. 8, 2009.

(51) Int. Cl.
A61K 31/522 (2006.01)
A61K 9/00 (2006.01)
A61K 9/70 (2006.01)
A61K 31/4985 (2006.01)

(52) U.S. Cl.
CPC ............ A61K 9/006 (2013.01); A61K 9/7007 (2013.01); A61K 31/4985 (2013.01)

(58) Field of Classification Search
CPC .................................................. A61K 31/522
USPC ......................................... 514/249; 424/443
See application file for complete search history.

(56) References Cited

U.S. PATENT DOCUMENTS

| | | |
|---|---|---|
| 3,753,732 A | 8/1973 | Boroshok |
| 3,819,706 A | 6/1974 | Mehta |
| 3,851,648 A | 12/1974 | Brooke |
| 4,136,145 A | 1/1979 | Fuchs et al. |
| 4,136,162 A | 1/1979 | Fuchs et al. |
| 4,572,832 A | 2/1986 | Kigasawa et al. |
| 4,662,880 A | 5/1987 | Hamel et al. |
| 4,690,825 A | 9/1987 | Won |
| 4,713,239 A | 12/1987 | Babaian et al. |
| 4,792,452 A | 12/1988 | Howard et al. |
| 4,839,177 A | 6/1989 | Colombo et al. |
| 4,842,854 A | 6/1989 | Babaian et al. |
| RE33,093 E | 10/1989 | Schiraldi et al. |
| 4,871,549 A | 10/1989 | Ueda et al. |
| 4,900,552 A | 2/1990 | Sanvordeker et al. |
| 4,921,695 A | 5/1990 | Babaian et al. |
| 4,925,670 A | 5/1990 | Schmidt |
| 4,957,745 A | 9/1990 | Jonsson et al. |
| 5,004,595 A | 4/1991 | Cherukuri et al. |
| 5,005,300 A | 4/1991 | Diaz et al. |
| 5,047,244 A | 9/1991 | Sanvordeker et al. |
| 5,081,154 A | 1/1992 | Appelgren et al. |
| RE33,994 E | 7/1992 | Baker et al. |
| 5,169,638 A | 12/1992 | Dennis et al. |
| 5,234,957 A | 8/1993 | Mantelle |
| 5,244,677 A | 9/1993 | Kreckel et al. |
| 5,332,576 A | 7/1994 | Mantelle |
| 5,342,627 A | 8/1994 | Chopra et al. |
| 5,354,551 A | 10/1994 | Schmidt |
| 5,358,970 A | 10/1994 | Ruff et al. |
| 5,391,377 A | 2/1995 | Barnwell |
| 5,399,358 A | 3/1995 | Baichwal et al. |
| 5,399,362 A | 3/1995 | Baichwal et al. |
| 5,422,123 A | 6/1995 | Conte et al. |
| 5,427,798 A | 6/1995 | Ludwig et al. |
| 5,433,960 A | 7/1995 | Meyers |
| 5,446,070 A | 8/1995 | Mantelle |
| 5,456,920 A | 10/1995 | Matoba et al. |
| 5,462,749 A | 10/1995 | Rencher |
| 5,470,581 A | 11/1995 | Grillo et al. |
| 5,541,231 A | 7/1996 | Ruff et al. |
| 5,601,842 A | 2/1997 | Bartholomaeus |
| 5,700,478 A | 12/1997 | Biegajski et al. |

(Continued)

FOREIGN PATENT DOCUMENTS

| | | |
|---|---|---|
| AU | 601478 | 9/1990 |
| AU | 7549696 | 7/1997 |
| CA | 2137017 | 5/1995 |
| CA | 2197941 | 8/1997 |
| CA | 2702614 | 4/2009 |
| CN | 101396364 | 4/2009 |
| DE | 2148159 | 8/1972 |
| EP | 0109269 | 5/1984 |
| EP | 0250187 | 12/1987 |
| EP | 0273069 | 7/1988 |
| EP | 0452446 | 10/1991 |

(Continued)

OTHER PUBLICATIONS

Chemical Abstracts, vol. 97, 1982, p. 487, Abstract No. 4931e, Columbus, Ohio, USA.

(Continued)

Primary Examiner — San-Ming Hui
(74) Attorney, Agent, or Firm — Butzel Long

(57) ABSTRACT

Improved pharmaceutical solid oral film dosage forms for the buccal and/or sublingual delivery of pharmaceutical, nutraceutical or cosmetic ingredients are endowed with instant hydration potential and complete dissolution potentially enabling the active ingredient to become immediately available for enhanced buccal and/or sublingual absorption and/or reduced absorption through the gastrointestinal route. The improved delivery systems for solubilizing and stabilizing pharmaceutically active ingredients exhibit enhanced stability by the use of a combination of crystallization inhibitors, which together can maintain the active ingredient in a desired plurality of particles in an effective size range within a polymeric film matrix.

30 Claims, No Drawings

(56) References Cited

U.S. PATENT DOCUMENTS

| | | | |
|---|---|---|---|
| 5,731,000 A | 3/1998 | Ruff et al. | |
| 5,763,493 A | 6/1998 | Ruff et al. | |
| 5,783,212 A | 7/1998 | Fassihi et al. | |
| 5,853,760 A | 12/1998 | Cremer | |
| 5,859,006 A | 1/1999 | Daugan | |
| 5,876,744 A * | 3/1999 | Della Valle | A61K 8/732 424/434 |
| 5,948,430 A | 9/1999 | Zerbe | |
| 5,955,126 A | 9/1999 | Jon et al. | |
| 5,968,553 A | 10/1999 | Maitra et al. | |
| 6,033,686 A | 3/2000 | Seth | |
| 6,096,341 A | 8/2000 | Seth | |
| 6,120,803 A | 9/2000 | Wong et al. | |
| 6,140,329 A | 10/2000 | Daugan | |
| 6,143,327 A | 11/2000 | Seth | |
| 6,153,223 A | 11/2000 | Apelian et al. | |
| 6,162,466 A | 12/2000 | Licht et al. | |
| 6,177,096 B1 | 1/2001 | Zerbe et al. | |
| 6,197,827 B1 | 3/2001 | Cary | |
| 6,221,917 B1 | 4/2001 | Maitra et al. | |
| 6,231,957 B1 | 5/2001 | Zerbe et al. | |
| 6,242,496 B1 | 6/2001 | Kulkarni et al. | |
| 6,248,363 B1 | 6/2001 | Patel et al. | |
| 6,254,886 B1 | 7/2001 | Fusca et al. | |
| 6,267,985 B1 | 7/2001 | Chen et al. | |
| 6,270,805 B1 | 8/2001 | Chen et al. | |
| 6,284,264 B1 | 9/2001 | Zerbe et al. | |
| 6,287,603 B1 | 9/2001 | Prasad et al. | |
| 6,306,436 B1 | 10/2001 | Chungi et al. | |
| 6,309,668 B1 | 10/2001 | Bastin et al. | |
| 6,333,332 B1 | 12/2001 | Han et al. | |
| 6,342,249 B1 | 1/2002 | Wong et al. | |
| 6,368,626 B1 | 4/2002 | Bhatt et al. | |
| 6,383,513 B1 | 5/2002 | Watts et al. | |
| 6,462,237 B1 | 10/2002 | Gidwani et al. | |
| 6,482,987 B2 | 11/2002 | Kulkarni et al. | |
| 6,500,459 B1 | 12/2002 | Chhabra et al. | |
| 6,548,083 B1 | 4/2003 | Wong et al. | |
| 6,548,490 B1 | 4/2003 | Doherty, Jr. et al. | |
| 6,558,701 B2 | 5/2003 | Bartholomaeus et al. | |
| 6,566,504 B2 | 5/2003 | Bhattacharya et al. | |
| 6,569,463 B2 | 5/2003 | Patel et al. | |
| 6,592,887 B2 | 7/2003 | Zerbe et al. | |
| 6,596,298 B2 | 7/2003 | Leung et al. | |
| 6,652,882 B1 | 11/2003 | Odidi et al. | |
| 6,660,292 B2 | 12/2003 | Zerbe et al. | |
| 6,709,671 B2 | 3/2004 | Zerbe et al. | |
| 6,723,358 B1 | 4/2004 | van Lengerich | |
| 6,730,330 B2 | 5/2004 | Whittle et al. | |
| 6,761,903 B2 | 7/2004 | Chen et al. | |
| 6,780,871 B2 | 8/2004 | Glick et al. | |
| 6,797,283 B1 | 9/2004 | Edgren et al. | |
| 6,821,975 B1 | 11/2004 | Anderson et al. | |
| 6,855,334 B2 | 2/2005 | Bhatt et al. | |
| 6,884,790 B2 | 4/2005 | Pitha | |
| 6,893,660 B2 | 5/2005 | Li et al. | |
| 6,905,708 B2 | 6/2005 | Li et al. | |
| 6,906,043 B2 | 6/2005 | Awamura et al. | |
| 6,923,988 B2 | 8/2005 | Patel et al. | |
| 6,943,166 B1 | 9/2005 | Pullman et al. | |
| 6,958,326 B2 | 10/2005 | Backensfeld et al. | |
| 6,960,357 B2 | 11/2005 | Chopra | |
| 7,025,998 B2 | 4/2006 | Senin et al. | |
| 7,132,113 B2 | 11/2006 | Zerbe et al. | |
| 7,182,958 B1 | 2/2007 | Oren et al. | |
| 7,201,923 B1 | 4/2007 | van Lengerich | |
| 7,241,411 B2 | 7/2007 | Berry et al. | |
| 7,357,891 B2 | 4/2008 | Yang et al. | |
| 7,417,044 B2 | 8/2008 | Orman et al. | |
| 7,423,026 B2 | 9/2008 | Jarvinen et al. | |
| 7,592,328 B2 | 9/2009 | Jarho et al. | |
| 7,674,479 B2 | 3/2010 | Zerbe et al. | |
| 7,803,392 B2 | 9/2010 | Mumper et al. | |
| 2002/0048600 A1 | 4/2002 | Bhatt et al. | |
| 2003/0003113 A1 | 1/2003 | Lewandowski | |
| 2003/0022912 A1 * | 1/2003 | Martino | A61K 9/0043 514/292 |
| 2003/0044462 A1 | 3/2003 | Subramanian et al. | |
| 2003/0054031 A1 | 3/2003 | Li et al. | |
| 2003/0144324 A1 | 7/2003 | Fox et al. | |
| 2003/0161874 A1 | 8/2003 | Li et al. | |
| 2003/0206942 A1 * | 11/2003 | Kulkarni et al. | 424/443 |
| 2004/0037883 A1 | 2/2004 | Zhou et al. | |
| 2004/0044005 A1 | 3/2004 | Cary | |
| 2004/0101556 A1 | 5/2004 | Li et al. | |
| 2004/0228915 A1 | 11/2004 | Noack et al. | |
| 2005/0112198 A1 | 5/2005 | Challapalli et al. | |
| 2005/0142195 A1 | 6/2005 | Li et al. | |
| 2005/0186257 A1 * | 8/2005 | Manegold et al. | 424/443 |
| 2005/0214371 A1 | 9/2005 | Di Capua et al. | |
| 2005/0232990 A1 | 10/2005 | Boehm et al. | |
| 2005/0244502 A1 | 11/2005 | Mathias et al. | |
| 2005/0250838 A1 | 11/2005 | Challapalli et al. | |
| 2005/0266072 A1 | 12/2005 | Oshlack et al. | |
| 2006/0020040 A1 | 1/2006 | Chawla et al. | |
| 2006/0034937 A1 | 2/2006 | Patel | |
| 2006/0099260 A1 | 5/2006 | Chow et al. | |
| 2006/0160888 A1 | 7/2006 | Kottayil et al. | |
| 2006/0165770 A1 | 7/2006 | Zhang | |
| 2006/0165779 A1 | 7/2006 | Chawla et al. | |
| 2006/0204571 A1 | 9/2006 | Dhavse et al. | |
| 2007/0104741 A1 | 5/2007 | Murty et al. | |
| 2007/0105909 A1 | 5/2007 | Bradley et al. | |
| 2007/0190144 A1 | 8/2007 | Zerbe et al. | |
| 2008/0009502 A1 | 1/2008 | Zalit et al. | |
| 2008/0026060 A1 | 1/2008 | Zerbe et al. | |
| 2009/0047330 A1 | 2/2009 | Bangalore | |
| 2009/0098211 A1 | 4/2009 | Zalit et al. | |
| 2009/0214602 A1 | 8/2009 | Goldsmith et al. | |
| 2009/0221667 A1 * | 9/2009 | Reddy | A61K 31/40 514/423 |
| 2010/0179159 A1 | 7/2010 | Alles et al. | |
| 2011/0028431 A1 | 2/2011 | Zerbe et al. | |
| 2011/0263606 A1 | 10/2011 | Zerbe et al. | |
| 2013/0137698 A1 | 5/2013 | Zerbe et al. | |

FOREIGN PATENT DOCUMENTS

| | | |
|---|---|---|
| EP | 1020184 | 7/2000 |
| EP | 1875914 | 9/2008 |
| GB | 853378 | 11/1960 |
| GB | 2048642 | 12/1980 |
| WO | 9215289 | 9/1992 |
| WO | 9503791 | 2/1995 |
| WO | 9820862 | 5/1998 |
| WO | 9830208 | 7/1998 |
| WO | 9932107 | 1/1999 |
| WO | 0021504 | 4/2000 |
| WO | 0066099 | 11/2000 |
| WO | 0180824 | 11/2001 |
| WO | 03086362 | 10/2003 |
| WO | 2004064815 | 5/2004 |
| WO | 2004047809 | 6/2004 |
| WO | 2004087175 | 10/2004 |
| WO | 2004110422 | 12/2004 |
| WO | 2005092297 | 6/2005 |
| WO | 2005077332 A2 | 8/2005 |
| WO | 2007002125 | 1/2007 |

OTHER PUBLICATIONS

Chemical Abstracts, vol. 100, 1984, p. 530, Abstract No. 137715q, Columbus, Ohio, USA.

Patent Abstracts of Japan, JP-A-57028102 (Sanei Chem Ind Ltd.), Feb. 15, 1982.

Munjal et al. "Polymeric Systems for Amorphous Δ9-Tetrahydrocannabinol Produced by a Hot-Melt Method." Part II: Effect of Oxidation Mechanisms and Chemical Interactions on Stability, Journal of Pharmaceutical Sciences, vol. 95, No. 11, Nov. 2006.

Munjal et al. "Chemical Stabilization of a Δ9-Tetrahydrocannabinol Prodrug in Polymeric Matrix Systems Produced by a Hot-Melt Method: Role of Microenvironment pH," AAPS PharmSciTech 2006, 7 (3) Article 71.

(56) References Cited

OTHER PUBLICATIONS

Hirayama et al. "Cyclodextrin-based Controlled Drug Release System," Advanced Drug Delivery Reviews 36, 1999, pp. 125-141.
Gao et al.: CN 101396364 A; Apr. 1, 2009 (English Machine Translation).
Patent Abstract of CN 101396364 (A), date of publication: Apr. 1, 2009.
Mannila et al., "Effects of RM-β-CD on sublingual bioavailability of Δ9-tetrahydrocannabinol in rabbits," (European Journal of Pharmaceutical Sciences 26 (2005) 71-77.
Communication from the European Patent Office dated Sep. 11, 2013 regarding a Supplementary European Search Report.
Reintjes T., Title: "Solubility Enhancement with BASF Pharma Polymers," published Oct. 2011 by BASF, the Chemical Company.
Stupak et al., Title: "Enhanced Absorption of Digitoxin from Orally Administered Digitoxin—Polyvinylpyrrolidone Coprecipitates," Journal of Pharmaceutical Sciences, vol. 62(11), pp. 1806-1809, published Nov. 1973.
International Search Report and Written Opinion, Sep. 7, 2011, from International Application No. PCT/IB2011/000882.
Patent Abstract of AU601478, date of publication Sep. 13, 1990.
Patent Abstract of AU7549696, date of publication, Jul. 3, 1997.
Patent Abstract of DE2148159, date of publication, Aug. 17, 1972.
Patent Abstract of EP0109269, date of publication, May 23, 1984.
Patent Abstract of EP0250187, date of publication, Dec. 23, 1987.
Patent Abstract of EP0273069, date of publication, Jul. 6, 1988.
Patent Abstract of EP0452446, date of publication, Oct. 23, 1991.
Patent Abstract of GB853378, date of publication, Nov. 9, 1960.
Patent Abstract of GB2048642, date of publication, Dec. 17, 1980.
Patent Abstract of WO9215289, date of publication, Sep. 17, 1992.
Patent Abstract of WO9820862, date of publication, May 22, 1998.
Patent Abstract of EP1020184, date of publication, Jul. 19, 2000.
Patent Abstract of WO0180824, date of publication, Nov. 1, 2001.
Patent Abstract of WO03086362, date of publication, Oct. 23, 2003.
Patent Abstract of WO2004110422, date of publication, Dec. 23, 2004.
Patent Abstract of WO0066099, date of publication, Nov. 9, 2000.
Patent Abstract of WO2007002125, date of publication Jan. 4, 2007.
Patent Abstract of CA2137017, date of publication, May 31, 1995.
Patent Abstract of CA2197941, date of publication, Aug. 20, 1997.
Patent Abstract of CA2702614, date of publication, Apr. 23, 2009.
Patent Abstract of CN101396364, date of publication, Apr. 1, 2009.
Patent Abstract of EP1875914, date of publication, Jan. 9, 2008.
Patent Abstract of WO0021504, date of publication, Apr. 20, 2000.
Patent Abstract of WO2004047809, date of publication, Jun. 10, 2004.
Patent Abstract of WO2004064815, date of publication, Aug. 5, 2004.
Patent Abstract of WO2004087175, date of publication, Oct. 14, 2004.
Patent Abstract of WO2005092297, date of publication, Oct. 6, 2005.
Patent Abstract of WO2005077332, date of publication, Aug. 25, 2005.
Patent Abstract of WO9503791, date of publication, Feb. 9, 1995.
Patent Abstract of WO9830208, date of publication, Jul. 16, 1998.
Patent Abstract of WO9932107, date of publication, Jul. 1, 1999.

* cited by examiner

SOLID ORAL FILM DOSAGE FORMS AND METHODS FOR MAKING SAME

CROSS REFERENCE TO RELATED APPLICATION

This application claims benefit under 35 U.S.C. Section 119(e) of provisional application Ser. No. 61/267,626, filed Dec. 8, 2009, entitled SOLID ORAL FILM DOSAGE FORMS AND METHODS FOR MAKING SAME, and is a division of U.S. application Ser. No. 12/963,132, filed Dec. 8, 2010, the entire contents of which are incorporated herein in their entirety.

FIELD OF THE INVENTION

This invention relates to solid oral pharmaceutical film dosage forms and more particularly to buccal and/or sublingual oral dosage forms comprised of at least one pharmaceutically active ingredient present as a stabilized plurality of particles.

BACKGROUND OF THE INVENTION

An oral film is a solid oral dosage form containing at least one water soluble polymer in combination with other acceptable ingredients and can provide therapeutic, nutritional and/or cosmetic effects. The polymeric matrix carrying the pharmaceutical, nutritional and/or cosmetic ingredient(s) is molded in a thin layer of variable area and shape. In contrast to conventional oral dosage forms, the administration of an oral film does not require water. A preferred site of administration is the buccal cavity. The solid oral dosage film can be placed on the tongue, on the cheek pouch, under the tongue or in the inner labial mucosa. The film is designed to deliver a drug in a manner that facilitates absorption of the drug. Oral film technology may be the preferred solid dosage option when aiming for a rapid onset of action and avoidance of the 'first-pass effect' (hepatic metabolism). It can also be used when compliance of the patient is an issue and/or concern. Pediatric and geriatric patients, or those with swallowing issues, will benefit the most through the use of orally disintegrating film technology, and oral film dosage forms will be of particular convenience when a discrete administration is preferred.

The pharmaceutically employed oral film is formulated to exhibit instant hydration followed by a rapid dissolution/disintegration upon administration into the oral cavity. Upon administration and dissolution, the patient will not feel any discomfort during and/or immediately after its dissolution. The disintegration time can be varied through the suitable adjustment of the composition and physical properties of the matrix. Film forming polymers of common pharmaceutical use are water-soluble or water dispersible polymers that conform to the required properties, including, but not limited to, film instant hydration potential, mucoadhesion and solubility over time. Examples of film forming polymers include cellulose derivatives, polyvinyl alcohol, polyvinyl pyrrolidone, starches, polyacrylates, gums (xanthane gum, arabic gum, guar gum, etc.) and/or mixtures thereof. Film forming polymers may be used in combinations chosen based on the desired characteristics of the delivery form (e.g., rapid disintegration, higher mucoadhesion, longer residence time, etc.).

There are many major difficulties and challenges associated with the manufacture of oral film dosage forms ranging from brittleness, tackiness, the hygroscopic nature and potential lack of homogeneity within the dosage form. Ideal physical characteristics of the oral film include dosage uniformity throughout, adequate flexibility and tensile strength to facilitate processing, handling, and packaging of the film in a consumer-friendly form. Attaining ideal conditions for one characteristic usually comes at the expense of other, often equally important, properties, resulting in a necessary compromise in various properties to achieve a working film dosage form. Therefore, the main challenges and obstacles encountered when using oral film technology as a pharmaceutical delivery vehicle are due to the very properties upon which oral film technology is based. For example, challenges are encountered when attempting to provide an oral dosage as a film exhibiting a high content of liquid ingredients (0-35% wt/wt), and high drug loading in a matrix which is formulated as a very thin (under 80 micron) and continuous, yet flexible film layer.

An important requirement of modem drug delivery technology is the formulation of a delivery system that is capable of achieving a desirable release profile for the ever increasing number of active pharmaceutical ingredients with limited to poor water solubility. There are many conventional approaches for increasing the degree of solubilization of poorly soluble drugs including formation of ionizable molecules, pH adjustment and the development of co-solvent systems. However these approaches can often be inadequate or inappropriate due to potential stability concerns. Particle size reduction has been a non specific formulation approach that can be applied to almost any drug to enhance solubility. Due to greatly enhanced surface area obtained in this way, the dissolution rate and the bioavailability of poorly water-soluble drugs are expected to be high. Once the solid dispersion is exposed to aqueous media and the carrier dissolved, the drug is released as very fine, colloidal particles which can dissolve and be absorbed more rapidly than larger particles.

The increase in surface area results in a significant increase in surface energy leading to greater solubilization. However the increase in surface energy is thermodynamically unfavorable and reagglomeration or crystallization/recrystallization of the particles is thermodynamically preferred resulting in a loss in the solubility of the material due to particle growth, and leading to decreased bioavailability. A preferred mechanism of stabilization of the reduced particles, for solid dosage forms, is physical stabilization of the particles through the dispersion of the particles on suitable polymers such as polyvinyl pyrrolidone, hydroxypropyl cellulose, hydroxypropylmethyl cellulose. This approach is often inadequate and leads to agglomeration and/or crystallization/recrystallization over time.

The key determinate properties in making an oral dosage film are the very particular features that facilitate the aggregation and/or crystallization to occur in an oral film relative to a classical solid dispersion (e.g. granulation, pellets, etc.). As discussed above, various technical approaches have been used to create solid solutions of a drug and to limit its reagglomeration or crystallization while increasing its bioavailability. Typically, the final product can have the shape of granules, pellets, or free flowing powder, and can subsequently be tableted or encapsulated. In the final product the amount of water or any liquid ingredient in a solid oral dosage form is typically less than 5%. The active ingredient is finely dispersed (sometimes down to a molecular level size) and is in very close contact with large polymers that physically limit reagglomeration of the active ingredient. However, these techniques are not suitable for the production of oral films characterized by a physical continuity of the matrix and a high level of liquid ingredients necessary to impart flexibility and tensile strength to the film. The resulting chemical environment allows the drug molecules a certain freedom to move and aggregate at a greater rate relative to other types of solid oral dosage forms. Reducing the amount of ingredients that impart flexibility to the oral film is undesirable, as it would result in a rigid matrix with reduced tensile strength and that is difficult to manufacture on a large scale. The recrystallization, agglomeration and/or aggregation phenomena must be avoided to maintain high drug bioavailability and to prevent an undesirable change in the physical characteristics of the film (strength, appearance, homogeneity, stability, etc).

A homogenous and stable distribution of the drug in the film matrix is of primary concern when developing an oral film for buccal delivery of a pharmaceutically active ingredient. Any increase in particle size due to aggregation and/or crystallization of the particles must be avoided to enhance transmucosal absorption and to limit the gastrointestinal absorption upon disintegration of the dosage form. It is well known that within the buccal cavity the amount of biological fluids (saliva) available for the solubilization of a drug is very limited as compared with the gastrointestinal fluids. Therefore any process promoting faster dissolution of the active ingredient is generally desirable, but increases the need for maintaining stability of the pharmaceutically active ingredient. In particular, stabilization of the reduced particle size is needed to facilitate effective transmucosal absorption. If the active ingredient were to agglomerate or to crystallize within the dosage form, its solubility will, correspondingly, decrease and will result in the active ingredient being swallowed with the saliva.

Another characteristic in determining the resistance of the drug to reagglomeration within films is the extremely thin physical continuity of the matrix which provides minimal physical resistance to particle migration, and makes it difficult to prevent reagglomeration of the pharmaceutically active ingredient. Further concern arising from conventional techniques is the increase in the susceptibility of the active to degradation due to the increase in available surface area.

The prior art does not fully address the difficulty associated with preparing a pharmaceutical oral film capable of delivering a film dosage form with stabilized increased solubility and enhanced bioavailability while maintaining essential film characteristics.

SUMMARY OF THE INVENTION

The solid dosage form described is an oral film for delivery of pharmaceutical, nutraceutical or cosmetic ingredients, with buccal delivery preferred. The film possesses an instant hydration potential, rapid dissolution and a stabilized increased water solubility of the active ingredient, thereby delivering the active ingredient available for immediate enhanced local absorption and consequently limiting loss or absorption later in the gastrointestinal route. The invention provides, among other things, improved delivery systems for solubilizing and stabilizing a plurality of pharmaceutically active ingredient particles in an effective particle size range that exhibit enhanced chemical stability, pharmaceutical formulations exhibiting improved bioavailability and/or absorption of pharmaceutically active ingredients when administered, and/or dosage forms for administration of pharmaceutically active ingredients achieved by the use of a combination of crystallization inhibitors, which together can maintain the active ingredient in a molecular dispersion within the polymeric film matrix. A description of the oral film manufacture is also disclosed.

DETAILED DESCRIPTION OF PREFERRED EMBODIMENT

The invention is generally directed to improved pharmaceutical oral dosage forms comprising at least one pharmaceutically active ingredient, a primary polymeric crystallization inhibitor, at least one liquid crystallization inhibitor, at least one plasticizer and optionally including at least one penetration enhancing substance, surfactant, sweetening agent, flavor, flavor enhancer, antioxidant, starch, and/or colorant, that provide improved characteristics such as those relating to disintegration, and drug absorption.

Unless otherwise noted, terms in this specification are intended to have their ordinary meaning in the relevant art.

The preferred embodiment of the invention includes the delivery of a wide range of pharmaceutically active ingredients within an oral film dosage form demonstrating a plurality of active ingredient particles within a desired size range. The particle size is synergistically stabilized by at least one primary crystallization inhibitor and at least one liquid crystallization inhibitor, where the combination of the stabilization effect of each inhibitor on particle growth is greater than the sum of their individual stabilizing effects in the solid oral film dosage forms.

The term "liquid crystallization inhibitor" refers to any substance that exists in a liquid state at a temperature of about 37° F. and that in combination with the primary crystallization inhibitor or inhibitors enhances the prevention and/or reduction of the rate of crystallization and/or agglomeration of the active substance or inhibits the growth of structural order (e.g., crystallization) of the active(s) in the film matrix over time and is mixable and/or compatible with the other excipients forming the film blend. The liquid crystallization inhibitor is present in the formulation in an amount that is effective for enhancing the prevention and/or reduction of crystallization and/or agglomeration of the active ingredient, and generally ranges from about 1% to 19% of the mass of the film dosage form. Certain non-limiting examples of liquid crystallization inhibitors include polyethylene glycols, polyoxyl glycerides, propylene glycol esters, diethylene glycol esters, glyceryl esters, polyoxyethylene sorbitan fatty acid esters, ethylene alkyl ethers, polyoxyethylene alkyl phenols, polyethylene glycol glycerol fatty acid esters, polyoxyethylene-polyoxypropylene block copolymers, polyoxyethylene glycerides, polyoxyethylene sterols, polyoxyethylene vegetable oils, and polyoxyethylene hydrogenated vegetable oils.

The amount of drug that can be incorporated in the film is generally from 0.01% to 50%, with preferred drug loading ranging from 1%-30% of the total weight of the film. Non-limiting examples of the pharmaceutically acceptable active ingredients that may be used in the invention include active ingredients that can exist in both amorphous and crystalline forms, such as hypnotics, sedatives, antiepileptics, awakening agents, psychoneurotropic agents, neuromuscular blocking agents, antispasmodic agents, antihistaminics, antiallergics, antidiarrhetics, cardiotonics, antiarrhythmics, diuretics, hypotensives, vasopressors, antitussive expectorants, thyroid hormones, sexual hormones, antidiabetics, antitumor agents, antibiotics and chemotherapeutics, and narcotics.

The invention further provides, among other things, improved mechanisms to achieve a desired release profile for at least one pharmaceutically active ingredient. While a rapid solubilization of the pharmaceutically active ingredient(s) is preferred, various desired solubilization profiles (i.e. plots of the quantity or quantities of the pharmaceutically active ingredient(s) absorbed by a liquid medium or mediums at particular time points) can be achieved by adjusting the properties of and procedures for producing the film dosage form. For example, the combination of an effectively stabilized particle size range (for example ca. 50-500 nm) exhibiting rapid solubilization, with a separately prepared, distinct, effectively stabilized particle size range (for example ca. 100-900 μm) demonstrating a decreased rate of solubilization of the same active relative to the plurality of particles exhibiting rapid solubilization, produces a dosage form that initially delivers the active rapidly followed by a slower rate of delivery that can be sustained over an effective period of time, preferably, twenty to forty five minutes.

The increase in solubility is due to a combination of an increase in the surface energy of the active particles and the stabilization of such. Factors which contribute to the improved stability of the active include a surprising and unforeseeable ability of the invention to provide extensive physical and/or chemical protection to the active once distributed on a suitable solid oral film.

The term "solid oral dosage form" as used herein refers to a physical form of a predetermined amount of medication that may contain liquid or gaseous matter, but is primarily composed of solid matter having a higher Young's modulus and/or shear modulus than liquids.

The term "primary crystallization inhibitor" as used herein refers to a water soluble or water-dispersible, film-forming substance that is substantially chemically inert in the dosage form and is substantially chemically and biologically inert in the environment of use (e.g., buccal cavity), and has the effect of inhibiting growth and/or agglomeration of particles of a pharmaceutically active ingredient disposed in an oral film dosage form.

By employing suitable primary crystallization inhibitors, the particle growth and/or increase in the structural order of the pharmaceutically or therapeutically active ingredient can be inhibited during administration of the dosage form. Examples of primary crystallization inhibitors include polyvinyl pyrrolidone, polyethylene oxide and poloxamer. Film forming polymers that may be combined with the primary crystallization inhibitors include cellulose-derivatives, hydroxypropyl cellulose, hydroxyethyl cellulose, or hydroxypropylmethyl cellulose, carboxymethyl cellulose, and/or mixtures thereof. Other optional polymers include, carbomers, pregelatinized modified starch, polyvinyl alcohol, sodium alginate, polyethylene glycol, natural gums like xanthane gum, tragacantha, guar gum, acacia gum, arabic gum, carboxyvinyl copolymers. Suitable polymers may be employed in an amount ranging between 25% and 85% of the mass of the film dosage form.

The term plasticizer as used to describe and claim certain embodiments of the invention refers generally to a chemical entity that, when present, reduces the glass-transition temperature of amorphous polymers. In particular, the present invention incorporates a plasticizer to impart flexibility, enhance elasticity and decrease brittleness. Preferred plasticizers include triacetin, citrate derivatives (such as triethyl, tributyl, acetyl tributyl, acetyl triethyl, trioctyl, acetyl trioctyl, trihexyl citrate, etc.) and dibutyl sebacate. An amount of plasticizer that may be used is from about 2% to about 25% of the mass of the film dosage form.

The term "stabilized" as used herein refers to inhibition or retardation of changes of volume and/or loss of surface area, and/or increases in structural order of the plurality of active particles. More specifically, in the presence of certain macromolecules or polymers, the material shows an improved lifetime in an optimal particle size range, as characterized by reduced rate of agglomeration, increased structural order, crystallization and/or recrystallization of therapeutically active ingredient, as to demonstrate a desired solubilization profile in a preferred liquid medium.

The term "penetration enhancer" as used herein to describe and claim the invention refers to a substance that can increase buccal permeation of an active ingredient by enabling a transcellular route for transportation of the drug through the buccal epithelium. Certain non-limiting examples of pharmaceutically acceptable penetration enhancers include benzalkonium chloride, cetylpyridinium chloride, cyclodextrins, dextran sulfate, lauric acid/propylene glycol, menthol, oleic acid, oleic acid derivatives, polyoxyethylene, polysorbates, sodium EDTA, sodium lauryl sulfate, sodium salicylate.

The term "surfactant" as used to describe and claim certain embodiments of the invention refers generally to a chemical compound or substance that, when present in an effective amount, reduces the surface tension of a liquid and the interfacial tension between liquids.

The invention may be prepared by first dispersing, suspending and/or dissolving at least one therapeutically active ingredient and an optional antioxidant or antioxidants in at least one solvent. One or more liquid crystallization inhibitors are added, together with one or more plasticizers, optionally one or more penetrations enhancers and/or one or more optional surfactants. The film forming polymers are added and the mixture is kept under rotation until the film forming polymers have completely dissolved and a homogenous blend has been obtained. Optional ingredients such as flavors, sweetener, taste maskers, antioxidants and colorants can be added at any time. It is preferred that the addition of other non active ingredients is completed at an appropriate time as to minimize potential segregation, physical-chemical incompatibility or partial dissolution of the film forming polymers.

The final viscosity of the blend affects the film casting potential. Optimal viscosity ranges from 2000 centipoises to 90,000 centipoises. The final blend is transferred onto a surface of a suitable carrier material and dried to form a film. The carrier material must have a suitable surface tension in order to facilitate the homogenous distribution of the polymer solution across the intended coating width, without the formation of a destructive bond between the film and the carrier. Examples of suitable materials include non-siliconized polyethylene terephthalate film, non-siliconized paper, polyethylene-impregnated kraft paper, and non-siliconized polyethylene film. The transfer of the solution onto the carrier material can be performed using any conventional film coating equipment. A suitable coating technique would involve a knife-over-roll coating head. The thickness of the resulting film depends on the concentration of solids in the coating solution and on the gap of the coating head and can vary between 1 and 500 μm. Drying of the film may be carried out in a high-temperature air-bath using a drying oven, drying tunnel, vacuum drier, or any other suitable drying equipment. A desired dry film thickness of about 70 μm is typically targeted to facilitate the administration, drying and processing of the film. However, it is possible to make thinner and thicker films.

The following examples illustrate formulations, oral dosage forms and methods of preparing same in accordance with certain non-limiting aspects of the invention. All percentages in the examples are by weight unless otherwise indicated.

EXAMPLE 1

About 0.1 to about 5 g of a pharmaceutically active ingredient is dissolved in 11-29 ml of ethyl alcohol. To the resulting solution, 0.1 g of aspartame, 1.0 to 2.9 g of menthol/triacetine and 0.1-1.0 g of propylene glycol caprilate are added. Optionally 0.1 to 1 g of polysorbate 80 and 0.1 to 1 g of polyoxyglyceride is added to the mixture. After one hour of stirring at high speed, 4 to 6 g of polyvinyl pyrrolidone and 0.1 to 0.5 g of pregelatinized modified starch are added and the mixture is stirred until homogenous. About 2.0 to 3.0 g of hydroxypropyl cellulose is added to the mixture. The blend is stirred for one hour before adding 0.02-0.08 g of colorant Yellow #6. Mixing is continued until a homogenous polymeric solution is obtained. About 25-35% of the solution is coated onto a suitable carrier material, for example non-siliconized, polyethylene-coated kraft paper, using conventional coating/drying equipment. Coating gap and web speed are adjusted to achieve a dry film thickness between 10 and 200 μm. The cast film is dried at a temperature of about 65° C. to achieve a desired effectively stabilized particle size range for immediate solubilization and the web speed is adjusted to completely remove the solvents from the film. The remaining 65-75% of the solution is cast on top of the previous film to achieve a dry film thickness from 40 μm to 60 μm, and dried at a temperature of 25° C. to achieve the desired effectively stabilized particle size range for a reduced rate of solubilization. The resulting film, with an intended average residence time of 30 minutes, is peeled off the carrier web and cut into pieces of a shape and size suitable for the intended use.

EXAMPLE 2

About 0.3 g of a pharmaceutically active ingredient is dissolved in 2 ml to 15.0 ml of ethyl alcohol and 40 to 56 ml of water. To the solution, 0.08 g of Talin, 0.15 g of aspartame, 2.0 g to 3.5 g of 10% menthol/triethyl citrate, 0.5 g to 1.5 g of polysorbate 80 were added and the resulting mixture is stirred at high speed for 1.5 hours. Optionally, the mixture can include 0.1 to 1.0 g of polyethyleneoxide and/or 0.2 g to 0.5 g of sodium EDTA. From 8.0 g to 10.0 g of polyvinyl pyrrolidone is added and the mixture is stirred for one more hour. From 2.0 g to 4.5 g of hydroxypropyl methyl cellulose type E15 was added to the mixture. Optionally 0.5 g to 4.5 g of high molecular weight polyoxyethylene is added and the blend is stirred for one hour before adding 0.04 g of colorant Yellow #6 and 0.5 g of mint oil. Mixing is continued until a homogenous polymeric solution is obtained. The solution is coated onto a suitable carrier material, and dried at 15° C. for a time sufficient to remove the solvent

EXAMPLE 3

About 2.8 g of a pharmaceutically active ingredient is dissolved in up to 4.5 ml of ethyl alcohol and from 31 ml to 35 ml of water. To the mixture, 0.5 g of ascorbic acid, 0.5 g of aspartame, 1.5 to 3 g of 14% menthol/triacetine, up to 0.5 g of polysorbate 20, and optionally 0.7 g of propylene glycol caprilate are added and the resulting mixture is stirred at high speed for 1 hour. From 6.0 to 8.0 g of polyvinyl pyrrolidone, 1.0 to 2.5 g of polyethylene oxide 8000, and 0.2 g of pregelatinized modified starch are added to the mixture and stirred until it is homogenous. 1.0 g to 4.0 g of hydroxypropyl cellulose is added to the mixture. The blend is stirred for 1 hour before adding 0.04 g of colorant Blue #1. Mixing is continued until a homogenous polymeric solution is obtained. The solution is coated onto a suitable carrier material, and dried.

EXAMPLE 4

From 0.5 g to 0.7 g of two different pharmaceutically active ingredients are dissolved in 1.0 ml to 3.0 ml of acetone and 21 ml of water. To the resulting solution, 0.03 g of sucralose, 1.0 g to 2.0 g of triethyl citrate, 0.3 g of polysorbate 80, 0.5 g to 1.0 g of sodium phosphate dibasic and 0.1 g to 0.9 g of glyceryl mono oleate are added and the resulting mixture is stirred at high speed for 1 hour. From 4.0 g to 7.0 g of polyvinyl pyrrolidone and 0.2 g of pregelatinized modified starch are added and the mixture is stirred until homogenous. 1.0 g to 3.0 g of hydroxypropyl cellulose is added to the mixture. The blend is stirred for 3 hours before adding 0.02 g of colorant Yellow #5 and 0.2 g of vanilla flavor, mixed until homogenous, coated onto a suitable carrier material, and dried.

EXAMPLE 5

From 1.0 g to 2.0 g of pharmaceutically active ingredient and 0.1 g to 1.0 g of ascorbic acid are partially dissolved in a mixture of 19 ml of water, 4.2 g of 14% menthol/triacetine, and 2.0 g to 3.0 g of glyceryl mono oleate. To the suspension 0.05 g of sucralose is added and the resulting mixture is stirred at high speed for 1 hour. From 3.0 g to 4.0 g of polyvinyl pyrrolidone and 0.1 g of pregelatinized modified starch are added and the resulting mixture is stirred until homogenous. Optionally from 2.0 g to 3.0 g of hydroxypropyl cellulose are added to the mixture. The blend is stirred for 1 hour before adding 0.01 g of colorant Blue #1. Mixing is continued until a homogenous polymeric solution is obtained. The solution is coated onto a suitable carrier material, and dried as described for example 1.

EXAMPLE 6

A gastro-resistant granule preparation is made by combining a therapeutically active ingredient and a methacrylic polymer in a 2:1 to 1:2 weight to weight ratio, and optionally 1% to 5% of a disintegrant is placed in a jacketed bowl (i.e. mixer bowl) and mixed for homogenization. The jacket temperature is kept at about 65° C., the motor output is maintained at about 101-161 watts, and the mixer and chopper speeds are set to about 1500-1700 rpm. The jacket temperature is maintained at about 10° C. above the melting point range of the granulation liquid, which is obtained by heating a fatty alcohol or a mixture of fatty alcohols to about 55° C. Optionally, 1% to 10% of one or more surfactants by weight and/or 1% to 5% of disintegrant are added in the molten granulation liquid. The liquefied mixture is slowly added in portions to the preheated mixed powder blend, until the endpoint of the coating process is reached. After cooling down, the particle size of the granulated material is reduced to a dimension compatible with the thickness of the film to be cast. A suitable grinder is used to mill the granulated material. After screening, only the fraction under 0.5 mm is retained to be incorporated in the film blend.

A film blend is prepared by first dissolving one or more film forming polymers in pure water or in a mixture of water and 1% to 10% of organic solvents. The total concentration of polymers may be from about 20% to about 45% of the weight of the solution of which polyvinyl pyrrolidone is between 70% and 100% of the total weight of the polymers. Other ingredients added into the mixture include 2% to 5% of glyceryl mono oleate, 2% to 6% of tri-ethyl citrate, adequate amounts of taste maskers, sweeteners, flavors and colorants. The mixture is stirred until total dissolution of the polymers and homogenization of the ingredients is completed.

The viscosity of the blend is measured. Optimal values are from 30,000 to 45,000 centipoise. To the wet blend is added 1% to 50% w/w of the gastro resistant granules as described above. The resulting suspension is stirring for a minimum time sufficient to obtain a homogenous dispersion of the granules in the wet film blend. The solution is coated onto non-siliconized, polyethylene-coated kraft paper, using conventional coating/drying equipment. Coating gap and web speed is adjusted to achieve a dry film thickness between 100 and 300 μm. The drying temperature is 45-60° C. The resulting film is peeled off the carrier web and cut into pieces of a shape and size suitable for the intended use

EXAMPLE 7

From 1.0 g to 2.0 g of pharmaceutically active ingredient is dissolved in an acidified mixture of 10 ml of water, 0.2 g of triacetine and 0.1 g of polyethylene glycol. To the resulting solution, 0.1 g to 1.0 g of hydroxypropyl cellulose and 0.1 g to 2.0 g of a methacrylic acid copolymer demonstrating a pH-dependent solubility are added. The resulting suspension is stirred for 1 hour before adding 0.01 g of colorant Blue #1. The volume of water is adjusted to achieve a 20% solid weight content. Mixing is continued until a homogenous polymeric solution is obtained. The solution is spray dried onto sugar-starch pellets (e.g., SUGLETS®, 250-355 μm in size). To a pre-blended acidified solution containing 0.5 g of ascorbic acid, 0.5 g of aspartame, 1.5 g to 3 g of 14% menthol/triacetine, up to 0.5 g of polysorbate 20, and optionally 0.7 g of propylene glycol and/or 0.5 g caprilate, 6.0 g to 8.0 g of polyvinyl pyrrolidone, 1.0 g to 2.5 g of polyethylene oxide 8000, 0.2 g of pregelatinized modified starch and 0.04 g of colorant Blue #1 added. The spray-dried SUGLETS® pellets are suspended and mixed under high speed for 5-10 seconds or until homogenously distributed within the blend. The solution is coated onto a suitable carrier material 300 and 500 μm, and dried at a temperature of 55-80° C.

EXAMPLE 8

A formulation was developed for preparing solid oral film dosage forms for buccal and/or sublingual administration of a mixture containing tadalafil involving first the preparation of a tadalafil system that demonstrates increased aqueous solubility of the tadalafil for use in the preparation of the film using an aqueous solvent.

Increased Tadalafil Solubilization Part A.

From 0.5 g to 0.7 g of tadalafil is dispensed in 20.0 ml to 30.0 ml of acetone. To the resulting solution polyvinyl pyrrolidone is added slowly to a vortex at a mass required to precipitate the tadalafil and the polyvinyl pyrrolidone (1.0 to 5.0 g). The resulting precipitate is dried at 40° C. and then milled.

Preparation of Film in an Aqueous System Part B.

In 20-35 mL of water, 0.03 g of sucralose, 1.0 g to 2.0 g of triethyl citrate, 0.3 g of polysorbate 80, 0.5 g to 1.0 g of sodium phosphate dibasic and 0.1 g to 0.9 g of glyceryl mono oleate are added and the resulting mixture is stirred at high speed for 1 hour. Slowly add 4.0 g to 7.0 g of the product produced from part A containing the tadalafil demonstrating increased aqueous solubilization, and 0.2 g of pregelatinized modified starch are added and the mixture is stirred until homogenous. 1.0 g to 3.0 g of hydroxypropyl cellulose is added to the mixture. The blend is stirred for 3 hours before adding 0.02 g of colorant Yellow #5 and 0.2 g of vanilla flavor, mixed until homogenous, coated onto a suitable carrier material, and dried.

Modifications of the invention will occur to those skilled in the art and to those who make or use the invention. Therefore, it is understood that the embodiment(s) shown and described above are merely for illustrative purposes and not intended to limit the scope of the invention, which is defined by the following claims as interpreted according to the principles of patent law, including the doctrine of equivalents.

The invention claimed is:

1. An oral film dosage form that maintains a plurality of active ingredient particles in an effective particle size range to maintain reduced structural order, and/or improve solubility and bioavailability of the active, comprising:
   at least one pharmaceutically active ingredient in the form of amorphous particles that are capable of existing in crystalline form;
   at least one primary crystallization inhibitor present in an amount that inhibits crystallization, growth and agglomeration of the amorphous particles of the pharmaceutically active ingredient;
   propylene glycol caprylate in an amount that further enhances inhibition of crystallization, growth and agglomeration of the amorphous particles of the pharmaceutically active ingredient; and
   at least one plasticizer present in an amount that is effective to increase flexibility and elasticity of the film dosage form.

2. An oral film dosage form that maintains a plurality of active ingredient particles in an effective particle size range to maintain reduced structural order, and/or improve solubility and bioavailability of the active, comprising:
   at least one pharmaceutically active ingredient in the form of amorphous particles having at least two distinct particle size ranges including a first size range of 50-500 nm and a second size range of 100-900 μm, the amorphous particles capable of existing in crystalline form;
   at least one primary crystallization inhibitor present in an amount that inhibits crystallization, growth and agglomeration of the amorphous particles of the pharmaceutically active ingredient;
   at least one liquid crystallization inhibitor in an amount that further enhances inhibition of crystallization, growth and agglomeration of the amorphous particles of the pharmaceutically active ingredient, the at least one liquid crystallization inhibitor selected from propylene glycol caprylate, glyceryl monooleate, and polyethylene glycol; and
   at least one plasticizer present in an amount that is effective to increase flexibility and elasticity of the film dosage form, the at least one plasticizer selected from triethyl citrate, tributyl citrate, acetyl tributyl citrate, acetyl triethyl citrate, trioctyl citrate, acetyl trioctyl citrate, trihexyl citrate, dibutyl sebacate, or triacetine, wherein said composition further comprises at least one mucoadhesive polymer.

3. The dosage form of claim 2, wherein said primary crystallization inhibitor is selected from polyvinyl pyrrolidone, polyethylene oxide, or poloxamer.

4. The dosage form of claim 2, wherein said composition further comprises at least one surfactant.

5. The dosage form of claim 2, wherein said composition further comprises at least one penetration enhancer selected from benzalkonium chloride, cetylpyridinium chloride, cyclodextrins, dextran sulfate, lauric acid, propylene glycol, menthol, oleic acid, oleic acid derivatives, polyoxyethylene, polysorbates, sodium EDTA, sodium lauryl sulfate or sodium salicylate.

6. The dosage form of claim 2, wherein said composition further comprises at least one sweetener.

7. The dosage form of claim 2, wherein said composition further comprises at least one colorant.

8. The dosage form of claim 2, wherein said composition further comprises at least one taste masker.

9. The dosage form of claim 2, wherein said composition further comprises at least one antioxidant.

10. The dosage form of claim 2, wherein said composition further comprises at least one flavoring agent.

11. The dosage form of claim 2, wherein said composition further comprises at least one pharmaceutically acceptable excipient.

12. The dosage form of claim 2, wherein said pharmaceutically active ingredient is selected from: hypnotics, sedatives, antiepileptics, awakening agents, psychoneurotropic agents, neuromuscular blocking agents, antispasmodic agents, antihistaminics, antiallergics, antidiarrhetics, cardiotonics, antiarrhythmics, diuretics, hypotensives, vasopressors, antitussive expectorants, thyroid hormones, sexual hormones, antidiabetics, antitumor agents, antibiotics and chemotherapeutics, and narcotics.

13. An oral film dosage form demonstrating a solubilization profile of at least one active ingredient resulting from the combination of two or more distinct, effectively stabilized, particle size ranges, comprising:
   an active ingredient in the form of amorphous particles having at least two distinct particle size ranges including a first size range of 50-500 nm and a second size range of 100-900 μm, the amorphous particles capable of existing in crystalline form;
   at least one primary crystallization inhibitor present in an amount that inhibits crystallization, growth and agglomeration of the amorphous particles of the pharmaceutically active ingredient;
   at least one liquid crystallization inhibitor in an amount that further enhances inhibition of crystallization, growth and agglomeration of the amorphous particles of the pharmaceutically active ingredient the at least one liquid crystallization inhibitor selected from propylene glycol caprylate, glyceryl monooleate, and polyethylene glycol; and
   at least one plasticizer present in an amount that is effective to increase flexibility and elasticity of the film dosage form, the at least one plasticizer selected from triethyl citrate, tributyl citrate, acetyl tributyl citrate, acetyl triethyl citrate, trioctyl citrate, acetyl trioctyl citrate, trihexyl citrate, dibutyl sebacate, or triacetine.

14. The dosage form of claim 13, wherein said plasticizer is selected from triethyl, tributyl, acetyl tributyl, acetyl triethyl, trioctyl, acetyl trioctyl, trihexyl citrate, dibutyl sebacate, triacetine, or derivatives thereof.

15. The dosage form of claim 13, wherein said composition further comprises at least one surfactant.

16. The dosage form of claim 13, wherein said composition further comprises at least one penetration enhancer selected from benzalkonium chloride, cetylpyridinium chloride, cyclodextrins, dextran sulfate, laurie acid/propylene glycol, menthol, oleic acid, oleic acid derivatives, polyoxyethylene, polysorbates, sodium EDTA, sodium lauryl sulfate or sodium salicylate.

17. The dosage form of claim 13, wherein said composition further comprises at least one sweetener.

18. The dosage form of claim 13, wherein said composition further comprises at least one colorant.

19. The dosage form of claim 13, wherein said composition further comprises at least one taste masker.

20. The dosage form of claim 13, wherein said composition further comprises at least one antioxidant.

21. The dosage form of claim 13, wherein said composition further comprises at least one flavoring agent.

22. The dosage form of claim 13, wherein said composition further comprises at least one mucoadhesive polymer.

23. The dosage form of claim 13, wherein said composition further comprises at least one pharmaceutically acceptable excipient.

24. The dosage form of claim 13, wherein said pharmaceutically active ingredient is selected from: hypnotics, sedatives, antiepileptics, awakening agents, psychoneurotropic agents, neuromuscular blocking agents, antispasmodic agents, antihistaminics, antiallergics, antidiarrhetics, card iotonics, antiarrhythmics, diuretics, hypotensives, vasopressors, antitussive expectorants, thyroid hormones, sexual hormones, antidiabetics, antitumor agents, antibiotics and chemotherapeutics, and narcotics.

25. The dosage form of claim 1, in which the amount of the primary crystallization inhibitor is from 25% to 85% of the mass of the film dosage form.

26. The dosage form of claim 25, in which the amount of the liquid crystallization inhibitor is from 1% to 19% of the mass of the film dosage form.

27. The dosage form of claim 26, in which the amount of the plasticizer is from 2% to 25% of the mass of the film dosage form.

28. An oral film dosage form that maintains a plurality of active ingredient particles in an effective particle size range to maintain reduced structural order, and/or improve solubility and bioavailability of the active, comprising:
   at least one pharmaceutically active ingredient in the form of amorphous particles having at least two distinct particle size ranges including a first size range of 50-500 nm and a second size range of 100-900 μm, the amorphous particles capable of existing in crystalline form;
   at least one primary crystallization inhibitor present in an amount that inhibits crystallization, growth and agglomeration of the amorphous particles of the pharmaceutically active ingredient;
   at least one liquid crystallization inhibitor present in an amount effective to further enhance inhibition of crystallization, growth and agglomeration of the amorphous particles of the pharmaceutically active ingredient, the at least one liquid crystallization inhibitor selected from propylene glycol caprylate, glyceryl monooleate and polyethylene glycol; and
   at least one plasticizer present in an amount that is effective to increase flexibility and elasticity of the film dosage form, the at least one plasticizer selected from triethyl citrate, tributyl citrate, acetyl tributyl citrate, acetyl triethyl citrate, trioctyl citrate, acetyl trioctyl citrate, trihexyl citrate, dibutyl sebacate, or triacetine and in which the liquid crystallization inhibitor comprises from 1% to 19% of the mass of the film dosage form.

29. The film of claim 28, wherein the liquid crystallization inhibitor is propylene glycol caprylate.

30. The film of claim 28, wherein the liquid crystallization inhibitor is glyceryl monooleate.

\* \* \* \* \*